United States Patent [19]

Johnson

[11] 4,296,110

[45] Oct. 20, 1981

[54] ANTIHYPERTENSIVE I-SUBSTITUTED CYCLIC LACTAM-2-CARBOXYLIC ACIDS

[75] Inventor: Alexander L. Johnson, Wilmington, Del.

[73] Assignee: E. I. Du Pont de Nemours and Company, Wilmington, Del.

[21] Appl. No.: 201,471

[22] Filed: Oct. 28, 1980

[51] Int. Cl.$^3$ .................................. A61K ; C07D ; A61K

[52] U.S. Cl. ................... 424/244; 424/267; 424/274; 260/239.3 R; 260/326.42; 546/221; 546/243

[58] Field of Search ............ 260/239.3 R, 326.42; 546/243, 221; 424/244, 267, 274

[56] References Cited

U.S. PATENT DOCUMENTS 4,154,937  5/1979  Cushman et al. ............... 546/221
4,156,789  5/1979  Ondetti et al. .................. 546/221

OTHER PUBLICATIONS

Medicinal Chemistry Symposium held 18 Jun. 1980 at Rensselaer Polytechnic Institute, Troy, N.Y.
U.S. Patent Application 06/193,644, filed 3 Oct. 1980 (Applicant: Johnson).

*Primary Examiner*—Robert T. Bond

[57] ABSTRACT

1-Substituted cyclic lactam-2-carboxylic acids and their derivatives are useful as antihypertensive agents.

11 Claims, No Drawings ns
ANTIHYPERTENSIVE I-SUBSTITUTED CYCLIC LACTAM-2-CARBOXYLIC ACIDS

BACKGROUND OF THE INVENTION

This invention relates to acids and derivatives thereof having useful pharmaceutical properties. In particular, this invention relates to 1-substituted cyclic lactam-2-carboxylic acids and derivatives thereof which are useful as antihypertensive agents.

Many current antihypertensive agents produce unwanted side effects because of undesirable mechanisms of action. For example, phenoxybenzamine is an α-adrenergic receptor blocker, and reserpine is a catecholamine depletor. Each of these mechanisms of action is undesirable because serious side-effects are produced. There is a constant need for antihypertensive agents which do not produce these side effects, which have fewer side effects or which minimize such adverse side effects.

SUMMARY OF THE INVENTION

According to the present invention, there are provided compounds of Formula I, pharmaceutical compositions containing them, and methods of using them to treat hypertension in mammals.

$$R_4-CH-N-CH-CON\begin{array}{c}\\\end{array}\begin{array}{c}R_2\\|\\COR_3\end{array}\begin{array}{c}\\R_1\end{array}\begin{array}{c}COR\\|\\\end{array}\begin{array}{c}H\\(CH_2)_m\end{array} \quad (I)$$

where
R and $R_3$ are independently OH, $C_1$–$C_4$ alkoxy or $C_6H_5CH_2O$;
$R_1$ is H, $CH_3$, $C_2H_5$, $CF_3$, isobutyl, isoamyl, —$(CH_2)_n NHR_5$ or $$\begin{array}{c}NH\\||\\-(CH_2)_pNHC-NH_2;\end{array}$$

$R_2$ is H or $CH_3$;
$R_4$ is $C_1$–$C_{10}$ alkyl, —$(CH_2)_q C_6H_5$ or —$(CH_2)_r NH_2$;
$R_5$ is H or $C_1$–$C_4$ alkyl;
m is 2, 3 or 4;
  n is an integer from 1–6;
  p is an integer from 1–6;
  q is an integer from 0–6; and
  r is an integer from 1–6.
and pharmaceutically acceptable salts thereof.

PREFERRED COMPOUNDS

Preferred for their antihypertensive activity and/or ease of synthesis are those compounds of Formula I where, independently:
R is OH;
$R_1$ is $CH_3$ or —$(CH_2)_4NH_2$;
$R_2$ is H;
$R_3$ is OH, $OCH_3$, or $OC_2H_5$; and
$R_4$ is —$CH_2CH_2C_6H_5$ or —$(CH_2)_4NH_2$.
More preferred for the same reasons are those compounds where $R_4$ is —$CH_2CH_2C_6H_5$.
Most preferred for the same reasons are those compounds where R, $R_1$, $R_2$, $R_3$ and $R_4$ are simultaneously defined as the preferred definitions.

DETAILED DESCRIPTION OF THE INVENTION SYNTHESIS

The new compounds of this invention are obtained by either of the two following procedures:

A. An ester of the Formula II $$\begin{array}{c}O\\||\\HN\quad(CH_2)_m\\|\\COR'\end{array} \quad (II)$$

where
R' is $C_1$–$C_4$ alkoxy, preferably tert-butyloxy, or benzyloxy,
is converted to an alkali metal salt and is coupled with a suitable derivative of Formula III $$R_4'-CH-N-CH-COY\begin{array}{c}R_2'\\|\\\end{array}\begin{array}{c}\\|\\COR_3'\end{array}\begin{array}{c}\\R_1'\end{array} \quad (III)$$

in which
Y is ethoxycarbonyloxy, methoxycarbonyloxy, N-oxysuccinimidyl, 4-nitrophenoxy;
$R_1'$ is H, $CH_3$, $C_2H_5$, $CF_3$, isobutyl, isoamyl, $(CH_2)_n NR_5COOCH_2C_6H_5$, or $(CH_2)_p NH—C(=NH)NHNO_2$;
$R_2'$ is $CH_3$, carbobenzyloxy, or tert-butoxycarbonyl;
$R_3'$ is $C_1$–$C_4$ alkoxy or benzyloxy;
$R_4'$ is $C_1$–$C_{10}$ alkyl, —$(CH_2)_q C_6H_5$, or —$(CH_2)_p NH-COOCH_2C_6H_5$; and
$R_5$, m, n, p, q, and r are as previously defined.
The carbobenzyloxy, tert-butoxycarbonyl, nitro, tert-butyl and benzyl groups are standard protective groups for peptide synthesis and can be removed at an appropriate stage as taught by Bodansky, Klousner, and Ondetti, "Peptide Synthesis", Second Edition, 1976, Wiley, NY, the disclosure of which is herein incorporated by reference.

Compounds of Formula III can be prepared either by
(1) alkylation of an appropriate amino acid with an appropriate 2-halocarboxylic acid ester:

$$R_4'-CH-Q + R_2''NHCH-COY\begin{array}{c}\\|\\COR_3'\end{array}\begin{array}{c}\\|\\R_1'\end{array}$$
$$(IV)\qquad\qquad(V)$$

III, or $$R_4'-CH-NHR_2'' + Q-CH-COY\begin{array}{c}\\|\\COR_3'\end{array}\begin{array}{c}\\|\\R_1'\end{array}$$
$$(VI)\qquad\qquad(VII)$$

(2) reductive alkylation of an appropriate amino acid ester with an appropriate 2-oxocarboxylic acid by means of sodium cyanoborohydride or by catalytic hydrogenation:

$$R_4'-\underset{\underset{COR_3'}{|}}{C}=O + R_2''NH-\underset{\underset{R_1'}{|}}{CH}-COY$$

(VIII)   (V)

$$R_4'-\underset{\underset{COR_3'}{|}}{CH}-NHR_2'' + O=\underset{\underset{R_1'}{|}}{C}-COY$$

(VI)

→ III where

Q is halogen,
Y is OH, alkoxy, or benzyloxy;
$R''_2$ is H or $CH_3$,
$R'_3$ is alkoxy or benzyloxy.

For compounds III ($R''_2 = CH_3$), $R''_2$ can optionally be introduced subsequent to the coupling step by use of an appropriate methylation agent, e.g., methyl iodide.

B. Alternatively, the compounds of this invention can be prepared by alkylation of a compound of Formula IX.

$$R_2NH-\underset{\underset{R_1'}{|}}{CH}-CO-N\underset{\underset{COR'}{\diagdown}}{\diagup}(CH_2)_m$$ (IX)

where

R' is alkoxy, preferably tert-butyloxy, benzyloxy, or OH;
$R'_1$ is H, $CH_3$, $C_2H_5$, $CF_3$, isobutyl, isoamyl, $(CH_2)_nNR_5COOCH_2C_6H_5$, or $(CH_2)_pNH-C(=NH)NHNO_2$; and
$R_2$ is H or $CH_3$.

The alkylation can be effected either by alkylation of IX with a 2-halocarboxylic acid (or ester) of the Formula IV, or reductive alkylation with a 2-oxocarboxylic acid (or ester) of the Formula VIII. The protective groups (carbobenzyloxy, benzyl, and nitro) are removed by catalytic hydrogenation or (tert-butyoxycarbonyl) by treatment with trifluoroacetic acid.

Compounds of Formula IX can be prepared by acylation of the alkali metal salt of a compound of Formula II (R=OH) with a compound of Formula X.

$$R_2''-\underset{\underset{R_1'}{|}}{\overset{\overset{R_6}{|}}{N}}-CH-COY$$ (X)

in which $R_6$ is tert-butyloxycarbonyl or benzyloxycarbonyl, $R_1'$ and $R_2''$ are as defined above, and Y is halogen, ethoxycarbonyl, methoxycarbonyl, N-oxysuccinimidyl, 4-nitrophenoxy or 2, 4-dinitrophenoxy, followed by removal of $R_6$ with trifluoroacetic acid (if $R_6$ is tert-butyloxycarbonyl) or catalytic reduction (if $R_6$ is benzyloxycarbonyl). To prepare intermediates of Formula IX where R'=OH, compounds of Formula IX where R' = tert-butyloxycarbonyl or benzyl are deprotected by $CF_3COOH$ or catalytic hydrogenation, respectively. Depending on the particular meanings of $R_6$ and R', deprotection of both the amine and ester functions may be done sequentially or simultaneously.

The compounds of this invention may have one asymmetric carbon atom in the ring and from 1 to 2 asymmetric carbon atoms in the side chain, depending on the substitution pattern of $R_1$. These asymmetric carbon atoms are indicated by an asterisk in the following formula:

$$R_4-\overset{*}{\underset{\underset{COR_3}{|}}{C}H}-\overset{*}{\underset{\underset{R_1}{|}}{N}}-\overset{*}{C}H-CON\underset{O\diagup\underset{(CH_2)_m}{\diagdown}}{\diagdown}\overset{COR}{\underset{H}{|}}$$

Accordingly, the compounds of the invention exist in stereoisomeric forms or racemic forms thereof. All these stereoisomeric forms are within the scope of the invention. When racemic starting materials are used in the synthetic procedures, the stereoisomers obtained in the product can be separated by conventional procedures of recrystallization and chromatography. In general, the L-isomer of the cyclic acid is preferred.

The acidic compounds of the invention (R=OH) form basic salts with various inorganic and organic bases which are within the scope of the invention. Such salts include alkali metal salts such as sodium and potassium salts, ammonium salts, alkaline earth metal salts such as calcium and magnesium salts, salts with organic bases such as the lower aliphatic amines, benzylamine, dicyclohexylamine, and with basic amino acids such as arginine. Generally, non-toxic physiologically acceptable salts are preferred, although other salts are also useful, for example, the dicyclohexylamine salt.

The salts are formed in the conventional manner by reacting the free acid form (R=OH) of the product with one or more equivalents of the appropriate base providing the desired cation in a solvent or medium in which the salt is insoluble, or in the case of water, which can be removed by freeze drying. The free acid can be regenerated from the salt by using an aqueous mineral acid solution, for example, sodium bisulfate or sulfuric acid, followed by extraction with an organic solvent such as ethyl acetate, dichloromethane or chloroform, or by passing the aqueous solution of the salt through a cation exchange resin in the hydrogen form, for example, polystyrene sulfonic acid resin. If desired, the regenerated acid can be converted to another salt.

The preparation of the compounds of this invention is illustrated by the following examples. The following abbreviations are used in these examples:

BOC = tert-butoxycarbonyl
Z = carbobenzyloxy
$N_p$ = p-nitrophenyl
OSu = N-oxysuccinimidyl

EXAMPLES 1–10

General Procedures for Coupling Amino Acid Esters to Lactam Acid Tert-Butyl Esters To 0.1 mole of the tert-butyl ester of the lactam acid in toluene is added 0.1 mole of potassium tert-butoxide with stirring and ice-bath cooling. The appropriate protected amino acid ester (0.1 mole) is then added, and the mixture is allowed to warm to room temperature. When the reaction is complete, as indicated by thin layer chromatography, the mixture is evaporated, and the residue is purified by chromatography.

Basic reagents other than potassium tert-butoxide which can be used in this step include lithium hydride, n-butyllithium, potassium hydride, sodium hydride and lithium diisopropylamide. Suitable solvents include anhydrous solvents such as, but not limited to, toluene, ether, dioxan, tetrahydrofuran, 1,2-dimethoxyethane, N,N-dimethylformamide and dimethylsulfoxide.

The carbobenzyloxy, benzyl or nitro protective group is then removed by hydrogenation in the presence of palladium on charcoal; the tert-butyl ester and BOC groups are removed by treatment with trifluoroacetic acid.

TABLE 1

| Ex | Amino Acid Ester | Lactam | Protective Group Removal | N-(aminoacyl) Lactam Acid Product |
|----|------------------|--------|--------------------------|-----------------------------------|
| 1. | Z—NHCH$_2$COONp | [5-membered lactam, HN, COOt-Bu] | a. H$_2$/Pd/C  b. CF$_3$COOH | H$_2$NCH$_2$CON—[lactam]—COOH |
| 2. | BOC—NHCH(CH$_3$)COOSu | [5-membered lactam, HN, COOt-Bu] | CF$_3$COOH | H$_2$NCH(CH$_3$)CON—[lactam]—COOH |
| 3. | Z—NHCH(CH$_2$CH(CH$_3$)$_2$)COONp | [5-membered lactam, HN, COOt-Bu] | a. H$_2$/Pd/C  b. CF$_3$COOH | H$_2$NCH(CH$_2$CH(CH$_3$)$_2$)CON—[lactam]—COOH |
| 4. | BOC—NHCH((CH$_2$)$_4$NH—Z)COONp | [5-membered lactam, HN, COOt-Bu] | CF$_3$COOH | H$_2$N—CH((CH$_2$)$_4$NH—Z)CON—[lactam]—COOH |
| 5. | BOC—NH—CH((CH$_2$)$_3$NH—C(=N—NO$_2$)—NH$_2$)—COOSu | [5-membered lactam, HN, COOt-Bu] | CF$_3$COOH | NH$_2$CH((CH$_2$)$_3$NH—C(=N—NO$_2$)—NH$_2$)CON—[lactam]—COOH |
| 6. | Z—NH—CH(CH$_3$)COONp | [6-membered lactam, HN, COOt-Bu] | a. H$_2$/Pd/C  b. CF$_3$COOH | NH$_2$CH(CH$_3$)CON—[lactam]—COOH |
| 7. | Z—NHCH((CH$_2$)$_2$CH(CH$_3$)$_2$)COONp | [6-membered lactam, HN, COOt-Bu] | a. H$_2$/Pd/C  b. CF$_3$COOH | NH$_2$CH((CH$_2$)$_2$CH(CH$_3$)$_2$)CON—[lactam]—COOH |
| 8. | Z—NHCH(CF$_3$)COOSu | [6-membered lactam, HN, COOt-Bu] | a. H$_2$/Pd/C  b. CF$_3$COOH | NH$_2$CH(CF$_3$)CON—[lactam]—COOH |

TABLE 1-continued

| Ex | Amino Acid Ester | Lactam | Protective Group Removal | N-(aminoacyl) Lactam Acid Product |
|---|---|---|---|---|
| 9. | BOC—NHCH(CH$_3$)COOSu | 7-membered lactam, HN–C(=O), COOt-Bu substituent | CF$_3$COOH | 7-membered lactam with NH$_2$CH(CH$_3$)CON– and COOH |
| 10. | Z—NHCH(CH$_2$CH(CH$_3$)$_2$)COONp | 7-membered lactam, HN–C(=O), COOt-Bu substituent | a. H$_2$/Pd/C  b. CF$_3$COOH | 7-membered lactam with NH$_2$CH(CH$_2$CH(CH$_3$)$_2$)CON– and COOH |

The N-(aminoacyl)lactam acids may be converted to their corresponding esters by standard procedures.

EXAMPLES 11–15

General Procedures for Alkylating the N-(aminoacyl) Lactam Acids with 2-Halocarboxylic Acids (or Esters)

The 2-halocarboxylic acid (or esters) (0.1 mole) and N-(aminoacyl) lactam acid (0.1 mole) are heated with stirring in a suitable solvent such as dimethylformamide, dimethylsulfoxide, dimethylacetamide or 1,2-dimethoxyethane, in the presence of 0.1 mole of a suitable base on a steam bath. Bases which may be used include potassium carbonate, potassium bicarbonate and sodium carbonate. When the reaction is complete, as indicated by thin layer chromatography, the mixture is filtered and evaporated in vacuo. The residue is purified by chromatography.

TABLE 2

| Ex | 2-Halo Carboxylic Acid (or Ester) | N-(Aminoacyl) Lactam Acid | Product |
|---|---|---|---|
| 11. | CH$_3$CH$_2$CHBrCOOH | pyrrolidinone with H$_2$NCH$_2$CON– and COOH | pyrrolidinone with CH$_3$CH$_2$CH(COOH)—NHCH$_2$CON– and COOH |
| 12. | (CH$_3$)$_2$CH(CH$_2$)$_2$CHBrCOOC$_2$H$_5$ | pyrrolidinone with H$_2$NCH(CH$_3$)CON– and COOH | pyrrolidinone with (CH$_3$)$_2$CH(CH$_2$)$_2$CH(COOCH$_2$CH$_3$)NHCH(CH$_3$)CON– and COOH |
| 13. | C$_6$H$_5$(CH$_2$)$_2$CHBrCOOH | pyrrolidinone with H$_2$NCH(CH$_3$)CON– and COOH | pyrrolidinone with C$_6$H$_5$(CH$_2$)$_2$CH(COOH)NHCH(CH$_3$)CON– and COOH |
| 14. | C$_6$H$_5$(CH$_2$)$_2$CHBrCOOH | pyrrolidinone with H$_2$NCH[(CH$_2$)$_4$NH–Z]—CON– and COOH | [pyrrolidinone with C$_6$H$_5$(CH$_2$)$_2$CH(COOH)NHCH[(CH$_2$)$_4$NH–Z]—CON– and COOH] → (H$_2$/Pd/c) → pyrrolidinone with C$_6$H$_5$(CH$_2$)$_2$CHNH(COOH)—CH[(CH$_2$)$_4$NH$_2$]CON– and COOH |

TABLE 2-continued

| Ex | 2-Halo Carboxylic Acid (or Ester) | N-(Aminoacyl) Lactam Acid | Product |
|---|---|---|---|
| 15. | C$_6$H$_5$(CH$_2$)$_2$CHBrCOOH | [structure: H$_2$NCHCON-lactam with (CH$_2$)$_3$-NH-C(=NNO$_2$)-NH$_2$ side chain, COOH] | [C$_6$H$_5$(CH$_2$)$_2$CHNHCHCON-lactam with (CH$_2$)$_3$-NH-C(=NNO$_2$)-NHZ side chain, COOH groups] →H$_2$/Pd/c→ [C$_6$H$_5$(CH$_2$)$_2$CHNHCHCON-lactam with (CH$_2$)$_3$-NH-C(=NH)-NH$_2$ side chain, COOH groups] |

EXAMPLES 16–20

N-methyl derivatives of Examples 11–15 can be prepared by methylating those compounds with methyl iodide in a suitable solvent, e.g., methanol, ethanol, acetonitrile, or DMF, optionally in the presence of a base such as sodium carbonate or bicarbonate or potassium carbonate or bicarbonate. A mixture of formic acid and formaldehyde can also serve as an effective N-methylating agent. The N-methyl derivatives of 19 and 20 can be prepared by methylating prior to the hydrogenation step.

TABLE 3

| Ex | | | |
|---|---|---|---|
| 16. | CH$_3$CH$_2$CHNHCH$_2$CON-lactam (COOH) | CH$_3$I → | CH$_3$CH$_2$CHN(CH$_3$)CH$_2$CON-lactam (COOH) |
| 17. | (CH$_3$)$_2$CH(CH$_2$)$_2$CHNHCHCON-lactam, CH$_3$ branch, COOH | CH$_3$I → | (CH$_3$)$_2$CH(CH$_2$)$_2$—CH—N(CH$_3$)—CH(CH$_3$)—CON-lactam, COOH |
| 18. | C$_6$H$_5$(CH$_2$)$_2$CHNHCHCON-lactam, CH$_3$ branch, COOH | CH$_3$I → | C$_6$H$_5$(CH$_2$)$_2$CHN(CH$_3$)—CH(CH$_3$)CON-lactam, COOH |
| 19. | C$_6$H$_5$(CH$_2$)$_2$CHNHCHCON-lactam with (CH$_2$)$_4$-NH-Z side chain, COOH | CH$_3$I → | [C$_6$H$_5$(CH$_2$)$_2$CHN(CH$_3$)—CHCON-lactam with (CH$_2$)$_4$-NH-Z side chain, COOH] →H$_2$/Pd/c→ C$_6$H$_5$(CH$_2$)$_2$CHN(CH$_3$)—CHCON-lactam with (CH$_2$)$_4$-NH$_2$ side chain, COOH |

TABLE 3-continued

| Ex |  |
|---|---|
| 20. | 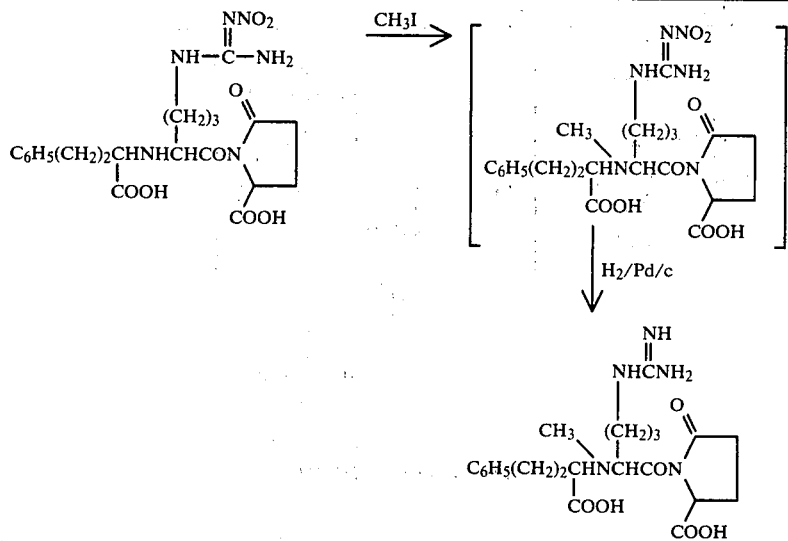 |

EXAMPLE 21

A solution of 0.02 mole sodium cyanoborohydride in 20 ml of methanol is added to a solution of 0.01 ml mole of sodium phenylpyruvate and 0.02 mole of the hydrochloride salt of N-(alanyl)-pyroglutamic acid (Ex. 2) in 20 ml of methanol, and the mixture is stirred for 48 hours at 25°. Conc. HCl (5 ml) is added, and after stirring one hour, the solution is evaporated in vacuo. The residue is dissolved in water; the pH is adjusted to 5–6; and the solution is again evaporated. The residue is purified by chromatography to give N[N'-(1-carboxy-2-phenyl)ethyl alanyl]pyroglutamic acid.

EXAMPLE 22

Substitution of ethyl pyruvate for the sodium phenylpyruvate of Ex. 21 gives N[N'-(1-carboxyethyl)-ethylalanyl]-pyroglutamic acid.

EXAMPLES 23–26

General Procedure for N-Alkylation of Amino Acids with 2-Halocarboxylic Acid Esters The amino acid (0.1 mole) and 2-halocarboxylic acid ester (0.1 mole) are heated with stirring in dimethylformamide in the presence of 0.1 mole of potassium bicarbonate on a steam bath. (The solvents and bases listed in Examples 11–15 are also suitable.) When the reaction is complete, as indicated by thin layer chromatography, the mixture is filtered and evaporated in vacuo. The residue is purified by chromatography.

TABLE 4

| Ex | 2-Halo Carboxylic Acid Ester | Amino Acid | Product |
|---|---|---|---|
| 23. | Cl<br>\|<br>CH₃CHCOOC₂H₅ | CH₃<br>\|<br>H₂NCHCOOH | CH₃<br>\|<br>CH₃CHNHCHCOOH<br>\|<br>COOC₂H₅ |
| 24. | Br<br>\|<br>CH₃CHCOOC₂H₅ | CH₃<br>\|<br>CH₃NCHCOOH | CH₃   CH₃<br>\|     \|<br>CH₃CHN——CH—COOH<br>\|<br>COOC₂H₅ |
| 25. | Br<br>\|<br>C₆H₅CH₂CH₂CHCOOC₂H₅ | Z—NH(CH₂)₄CH(NH₂)COOH | NHZ<br>\|<br>(CH₂)₄<br>\|<br>C₆H₅CH₂CH₂CHNHCHCOOH<br>\|<br>COOC₂H₅ |
| 26. | Br<br>\|<br>(CH₃)₂CH(CH₂)₂CHCOOC₂H₅ | N—NO₂<br>\|\|<br>NH₂—C—NH—(CH₂)₃CH(NH₂)COOH |  |

TABLE 4-continued

| Ex | 2-Halo Carboxylic Acid Ester | Amino Acid | Product |
|---|---|---|---|
| | | | $(CH_3)_2CH(CH_2)_2\underset{\underset{COOC_2H_5}{\mid}}{C}-NH-\underset{\underset{(CH_2)_3}{\mid}}{CH}-COOH$ <br> where the side chain is $(CH_2)_3-NH-\overset{\overset{N-NO_2}{\parallel}}{C}-NH_2$ |

EXAMPLES 27–29

General Procedure for Reductive N-Alkylation of Amino Acid Esters with 2-Oxocarboxylic Acids A mixture of the amino acid ester (0.1 mole) hydrochloride, sodium 2-oxocarboxylate (0.1 mole), and sodium cyanoborohydride (0.2 mole) in 500 ml of methanol is stirred at 25° for 48 hours. Conc. HCl (100 ml) is added, and after stirring for one hour, the solution is evaporated in vacuo. The residue is dissolved in water; the pH is adjusted to 5–6; and the solution is again evaporated. The residue is purified by chromatography.

EXAMPLES 30–32

General Procedure for Coupling the Products of Examples 27–29 to the 1-Position of Lactam Carboxylic Acids (or Esters)

To N-(1-carboalkoxy-alkyl) amino acid (cf. Exs. 27–29) (0.1 mole) and 0.2 mole of triethylamine in 300 ml of tetrahydrofuran is added with stirring in an ice bath with 0.2 mole of benzyl chloroformate. The mixture is stirred until precipitation of triethylamine hydrochloride is complete. The triethylamine hydrochloride is filtered off, and the filtrate is dropped into a stirred

TABLE 5

| Ex | Amino Acid Ester | 2-Oxocarboxylic Acid | Product |
|---|---|---|---|
| 27. | $(CH_3)_2CHCH_2\underset{\underset{NH_2}{\mid}}{CH}-COO-t-Bu$ | $CH_3COCOOH$ | $(CH_3)_2CHCH_2\underset{\underset{COOt-Bu}{\mid}}{CHNH}\underset{\underset{}{\mid}}{\overset{\overset{CH_3}{\mid}}{CH}}COOH$ |
| 28. | $C_6H_5CH_2CH_2\underset{\underset{NH_2}{\mid}}{CH}-COOC_2H_5$ | $CH_3CH_2COCOOH$ | $C_6H_5CH_2CH_2\underset{\underset{COOC_2H_5}{\mid}}{CHNH}\underset{\underset{}{\mid}}{\overset{\overset{CH_3}{\mid}}{CH}_2}CHCOOH$ |
| 29. | $Z-NH(CH_2)_4\underset{\underset{NH_2}{\mid}}{CH}-COOC_2H_5$ | $CH_3COCOOH$ | $Z-NH(CH_2)_4\underset{\underset{COOC_2H_5}{\mid}}{CHNH}\underset{\underset{}{\mid}}{\overset{\overset{CH_3}{\mid}}{CH}}COOH$ | mixture of 0.1 mole of the tert-butyl ester of the lactam acid and 0.1 mole of potassium tert-butoxide in tetrahydrofuran. (Other suitable bases and solvents are those listed in Examples 1–10). The protective groups are then removed by catalytic hydrogenation and $CF_3COOH$ treatment to give the desired products, which can be purified by chromatography.

TABLE 6

| Ex | N-(1-Carboalkoxy-alkyl)aminoacid | Lactam Acid | Product |
|---|---|---|---|
| 30. | $(CH_3)_2CHCH_2\underset{\underset{COOt-Bu}{\mid}}{CHNH}\overset{\overset{CH_3}{\mid}}{CH}COOH$ <br> (From Ex. 27) | 6-oxopiperidine-2-COOt-Bu | $(CH_3)_2CHCH_2\underset{\underset{COOt-Bu}{\mid}}{CH}-\overset{\overset{Z}{\mid}}{N}-\overset{\overset{CH_3}{\mid}}{CH}CO-HN\text{-lactam-COOt-Bu}$ <br> a. $H_2/Pd/c$ <br> b. $CF_3COOH$ |

TABLE 6-continued

| Ex | N-(1-Carboalkoxy-alkyl)aminoacid | Lactam Acid | Product |
|---|---|---|---|

(CH₃)₂CHCH₂CH—NH—CH(CH₃)—CON⟨ring⟩—COOH (ring with =O and COOH)

31. C₆H₅(CH₂)₂CHNHCHCOOH with CH₂CH₃ branch and COOC₂H₅ ; Lactam: HN-ring with =O and COOt-Bu ; Product: [C₆H₅(CH₂)₂CH(Z)NCHCON-ring, CH₂CH₃, COOC₂H₅, COOt-Bu] → a. H₂/Pd/c  b. CF₃COOH → C₆H₅(CH₂)₂CHNHCHCON-ring, CH₂CH₃, COOC₂H₅, COOH 32. Z—NH(CH₂)₄CHNHCHCOOH, CH₃, COOC₂H₅ ; Lactam: HN-ring =O, COOt-Bu ; Product: [Z—NH(CH₂)₄CH(Z)NCHCON-ring, CH₃, COOC₂H₅, COOt-Bu] → a. H₂/Pd/c  b. CF₃COOH → NH₂(CH₂)₄CHNHCHCON-ring, CH₃, COOC₂H₅, COOH

Dosage

The compounds of this invention can be administered in the treatment of hypertension according to the invention by any means that effects contact of the active ingredient compound with the site of action in the body of a warm-blooded animal. For example, administration can be parenteral, i.e., subcutaneous, intravenous, intramuscular, or intraperitoneal. Alternatively or concurrently, administration can be by the oral route.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Dosages as high as 100 milligrams per kilogram of body weight can be used. Usually, a daily dosage of active ingredient compound will be from about 0.1 to 100 milligrams per kilogram of body weight. Ordinarily, from about 0.05 to 80, and preferably about 1 to 40 milligrams per kilogram per day in one or more applications per day is effective to obtain desired results. For the more potent compounds of the invention, the daily dosage ranges are from about 0.01 to 10 mg/kg, preferably 0.05 to 10 mg/kg, and more preferably 0.05 to 5 mg/kg.

Dosage forms (compositions) suitable for internal administration contain from about 0.1 milligrams to about 500 milligrams of active ingredient per unit. In these pharmaceutical compositions, the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups and suspensions; it can also be administered parenterally, in sterile liquid dosage forms.

Gelatin capsules can contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text is this field.

Useful pharmaceutical dosage-forms for administration of the compounds of this invention can be illustrated as follows:

Capsules

A large number of unit capsules can be prepared by filling standard two-piece hard gelatin capsules each with 50 milligrams of powdered active ingredient, 175 milligrams of lactose, 24 milligrams of talc, and 6 milligrams magnesium stearate.

Capsules

A mixture of active ingredient in soybean oil can be prepared and injected by means of a positive displacement pump into gelatin to form soft gelatin capsules containing 50 milligrams of the active ingredient. The capsules can be washed in petroleum ether and dried.

Tablets

A large number of tablets can be prepared by conventional procedures so that the dosage unit is 50 milligrams of active ingredient, 6 milligrams of magnesium stearate, 70 milligrams of microcrystalline cellulose, 11 milligrams of cornstarch and 27.5 milligrams of lactose. Appropriate coatings can be applied to increase palatability or delay absorption.

Injectable

A parenteral composition suitable for administration by injection can be prepared by stirring 1.5% by weight of active ingredient in 10–60% by volume of co-solvents, like propyleneglycol in water. The resultant solution can be sterilized by filtration.

Suspension

An aqueous suspension can be prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Injectable

A parenteral composition suitable for administration by injection can be prepared by dissolving 1% by weight of active ingredient in sodium chloride injection U.S.P. XV and adjusting the pH of the solution to between 6 and 7. The solution can be sterilized by filtration.

Utility

The compounds of this invention inhibit the conversion of the decapeptide angiotensin I to the octapeptide angiotensin II, and are useful therefore in alleviating angiotensin induced hypertension. The enzyme renin acts on a blood plasma pseudoglobulin, angiotensinogen, to produce angiotensin I, which is then converted in the presence of angiotensin converting-enzyme (ACE) to angiotensin II. The latter substance is a powerful vasopressor agent which has been implicated as a causative agent for producing high blood pressure in various mammalian species, such as rats, dogs and humans. The compounds of this invention inhibit the action of ACE and this reduces the formation of the vasopressor agent angiotensin II. By administering a compound of this invention to a species of mammal with hypertension due to angiotensin, the blood pressure is reduced.

The potential antihypertensive effects of the compounds of this invention may be demonstrated by administering a compound to a rat and determining the vasopressor response to intravenous treatment with angiotensin I. These compounds inhibit ACE and reduce or prevent the usual vasopressor response to angiotensin I administration. In addition, the compounds lower blood pressure after administration to spontaneously hypertensive rats or to rats made hypertensive by constriction to a renal artery as suggested by Goldblatt (Goldblatt, H., et al., *Journal of Experimental Medicine*, 59, 347 (1939).

What is claimed is:

1. A compound of the formula:

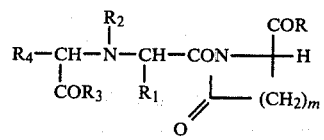

where
R and $R_3$ are independently OH, $C_1$–$C_4$ alkoxy or benzyloxy;
$R_1$ is H, $CH_3$, $C_2H_5$, $CF_3$, isobutyl, isoamyl, —$(CH_2)_n NHR_5$ or

$R_2$ is H or $CH_3$;
$R_4$ is $C_1$–$C_{10}$ alkyl, —$(CH_2)_q C_6 H_5$ or —$(CH_2)_r NH_2$;
$R_5$ is H or $C_1$–$C_4$ alkyl;
m is 2, 3 or 4;
n is an integer from 1–6;
p is an integer from 1–6;
q is an integer from 0–6; and r is an integer from 1–6;
and pharmaceutically acceptable salts thereof.

2. A compound of claim 1 where R is OH.

3. A compound of claim 1 where $R_1$ is $CH_3$ or —$(CH_2)_4NH_2$.

4. A compound of claim 1 where $R_2$ is H.

5. A compound of claim 1 where $R_3$ is OH, $OCH_3$ or $OC_2H_5$.

6. A compound of claim 1 where $R_4$ is —$CH_2CH_2C_6H_5$ or —$(CH_2)_4NH_2$.

7. A compound of claim 6 where $R_4$ is —$CH_2CH_2C_6H_5$.

8. A compound of claim 1 where R is OH, $R_1$ is $CH_3$ or —$(CH_2)_4NH_2$, $R_2$ is H, $R_3$ is OH, $OCH_3$ or $OC_2H_5$ and $R_4$ is —$CH_2CH_2C_6H_5$ or —$(CH_2)_4NH_2$.

9. A compound of claim 8 where $R_4$ is $CH_2CH_2C_6H_5$.

10. A pharmaceutical composition consisting essentially of a suitable pharmaceutical carrier and an effective hypertensive amount of a compound of claims 1 to 9.

11. A method of treating hypertension in mammals which comprises administering to the mammal an effective hypertensive amount of a compound of claims 1 to 9.

* * * * *